United States Patent [19]

Uchida et al.

[11] Patent Number: 5,318,798

[45] Date of Patent: Jun. 7, 1994

[54] PROCESS FOR PRODUCING KAMPO MEDICINE HARD CAPSULES

[75] Inventors: Toshihiro Uchida; Shin'ichiro Konishi; Takayoshi Kimura, all of Ibaraki, Japan

[73] Assignee: Tsumura & Co., Tokyo, Japan

[21] Appl. No.: 941,800

[22] Filed: Sep. 8, 1992

[30] Foreign Application Priority Data

Sep. 5, 1991 [JP] Japan .................................. 3-252747

[51] Int. Cl.⁵ .......................... A61K 9/48; B01J 13/02
[52] U.S. Cl. ............................... 427/213.35; 424/452; 424/456; 514/962; 514/974
[58] Field of Search ...................... 427/213.31, 213.35; 424/452, 456; 514/962, 974

[56] References Cited

U.S. PATENT DOCUMENTS

| | | | |
|---|---|---|---|
| 3,780,065 | 12/1973 | Sutton | 514/962 X |
| 3,909,444 | 9/1975 | Anderson et al. | 428/402.24 |
| 3,915,955 | 10/1975 | Cooper et al. | 514/962 X |
| 3,943,238 | 3/1976 | Kobayashi et al. | 424/456 |
| 4,719,228 | 1/1988 | Rawlins | 514/962 X |
| 4,806,659 | 2/1989 | Itsuo et al. | 549/399 |
| 5,221,289 | 6/1993 | Miyamatsu et al. | 435/190 X |

OTHER PUBLICATIONS

Nakagawa et al., "Effects of Particle Size of Rifampicin and Addition of Magnesium Stearate on Release of Rifampicin from Hard Gelatin Capsules," Yakugaku Zasshi, 11 (11) 1111–1117 (1980).

J. Pharm. Phrmac., The Effect Of Additives On The Release Of Drug From Hard Gelatin Capsules, vol. 23, pp. 452–453.

Primary Examiner—Richard D. Lovering
Attorney, Agent, or Firm—Sughrue, Mion, Zinn, Macpeak & Seas

[57] ABSTRACT

When a powdered extract of Kampo medicine is encapsulated as such in hard capsules, the pharmaceutical effects of the Kampo medicine cannot be fully achieved, since the dissolution of the content of the hard capsules requires a long period of time. Therefore, the present invention aims at providing Kampo medicine hard capsules having good dissolution properties.

The present invention provides a process for producing Kampo medicine hard capsules which comprises compacting Kampo medicine extract powder, mixing magnesium stearate with the compacted Kampo medicine extract powder and filing the mixture into gelatin hard capsules.

It is preferable that the weight ratio of the magnesium stearate to the Kampo medicine powdered extract ranges from 0.5/100 to 3/100. Furthermore, it is preferable that said Kampo medicine is selected from Orengedoku-to, Sho-saiko-to, Ninjin-to, San'o-shashin-to, Mao-bushi-saishin-to, Anchu-san, Keishi-bukuryo-gan, Byakko-ka-ninjin-to, Shakuyaku-kanzo-to and Sairei-to.

3 Claims, No Drawings

PROCESS FOR PRODUCING KAMPO MEDICINE HARD CAPSULES

FIELD OF THE INVENTION

This invention relates to a process for producing Kampo medicine hard capsules usable in the field of pharmaceuticals manufacturing.

BACKGROUND OF THE INVENTION

Kampo medicines are herbal medicines which originated from Chinese medicine and have been developed in Japan, and crude drugs (galenicals) have been applied to such Kampo medicines from ancient times. Recipes for these crude drugs based on experiences over a long time are described in a number of Chinese classical literatures such as *Shang Han Lun* and *Jin Kui Yao Lue*.

However, in the case of Kampo medicine prepared by cutting and decocting crude drugs to thereby extract active ingredients in accordance with these recipes, the preparation of Kampo medicine takes a long time and much labor each time on use. In addition, thus obtained decoctions have characteristic uncomfortable drug odors and tastes and, therefore, cannot be easily taken.

Therefore, in these days, Kampo medicine extract preparations are commonly used in the fields of nonproprietary drugs and ethical drugs and largely contribute to clinical pharmacy, although it is preferable to take the medicines in the form of the above-mentioned decoctions. This is because that these Kampo medicine extract preparations require no procedure for extracting active ingredients and can be easily stored and carried.

These Kampo medicine extract preparations are usually produced by the following method; a crude drug is cut into pieces and extracted with water or an alcohol; the obtained extract solution is concentrated, if required, and then dried to thereby give a powdered extract of the Kampo medicine; and the powdered extract is blended with appropriate fillers (for example, lactose, corn starch, crystalline cellulose) and formulated into a desired dosage forms such as tablets, capsules, powders, fine granules and granules.

Capsules are advantageous in that the content of an active ingredient in each capsule can be accurately controlled and that they can be easily formulated and conveniently carried. It is further advantageous to encapsulate Kampo medicine in hard capsules since the uncomfortable taste, odor and color of a principal agent can be masked and thus a product excellent in appearance can be obtained.

However, when a powdered extract of a Kampo medicine is encapsulated in hard capsules, the pharmaceutical effects of the Kampo medicine cannot be fully achieved, since the dissolution of the content of hard capsules requires a long period of time.

Under these circumstances, it has been required to develop Kampo medicine hard capsules having good dissolution properties.

SUMMARY OF THE INVENTION

The present inventors have conducted extensive studies in order to develop Kampo medicine hard capsules having good dissolution properties. As a result, they have successfully found that Kampo medicine hard capsules excellent in dissolution properties can be obtained by compacting powdered extract of Kampo medicine, adding magnesium stearate to the compacted powder of Kampo medicine extract and filing the mixture into gelatin capsules, thus completing the present invention.

Accordingly, the present invention provides the following processes.

(1) A process for producing Kampo medicine hard capsules, which comprises compacting Kampo medicine extract powder, mixing magnesium stearate with the compacted Kampo medicine extract powder and filing the mixture into gelatin hard capsules.

(2) A process as described in the above (1), wherein the weight ratio of the magnesium stearate to the compacted Kampo medicine extract powder ranges from 0.5/100 to 3/100.

(3) A process as described in the above (1), wherein the Kampo medicine is selected from Oren-gedoku-to, Sho-saiko-to, Ninjin-to, San'o-shashin-to, Mao-bushi-saishin-to, Anchu-san, Keishi-bukuryo-gan, Byakko-ka-ninjin-to, Shakuyaku-kanzo-to and Sairei-to.

DETAILED DESCRIPTION OF THE INVENTION

All the Kampo medicine usually used in the field of pharmaceutics can be used in the present invention without any restriction, involving so-called crude drugs and crude drug preparations containing one or more crude drugs, which are well known in the art in terms of the recipes and pharmaceutical efficacy thereof.

Suitable examples of Kampo medicine which can be used in the present invention are described, for example, in *Ippan Kampo Shoho no Tebiki* (*Handbook for Formulatinq Chinese Medicines for General Uses*) (supervised by Pharmaceutical Affairs Bureau, Ministry of Health and Welfare, published by Yakugyo Jiho K. K., Jan. 8, 1983, 4th and 6th ed.), *Tsumura Iryoyo Kampo Seizai* (*Tsumura's Recipes for Kampo Medicines*)" (catalogue) and Kampo (edited by Akira Tsumura, published by Japan Publications, Inc., 1991). Particular examples of the Kampo medicine include Anchu-san, Irei-to, Eppi-kajutsu-to, Oren-gedoku-to, Oren-to, Ogi-kenchu-to, Otsuji-to, Unkei-to, Unsei-in, Umpi-to, Kami-kihi-to, Kami-shoyo-san, Kakkon-to, Kakkon-to-ka-senkyu-shin'i, Kam-baku-taiso-to, Kihi-to, Kikyo-to, Gosha-jin-ki-gan, Keihi-to, Keishi-ka-ryukotsu-borei-to, Keishi-ka-shakuyaku-to, Keishi-ka-jutsubu-to, Keishi-ninjin-to, Keishi-to, Keishi-ka-shakuyaku-daio-to, Keishi-bukuryo-gan, Keishi-bukuryo-gan-ka-yokuinin, Keikyoso-so-o-shim-bu-to, Keigai-rengyo-to, Goko-to, Goshaku-san, Gorin-san, Gorei-san, Goshuyu-to, Kososan, San'o-shashin-to, Sammotsu-ogon-to, Jinso-in, Sansonin-to, Shigyaku-san, Shikunshi-to, Shimotsu-to, Jiinkokato, Jiin-shiho-to, Ji-daboku-ippo, Ji-zuso-ippo, Shichimotsu-koka-to, Saikan-to, Saiko-ka-ryukotsu-borei-to, Saiko-keishi-kankyo-to, Saiko-keishi-to, Saiko-seikan-to, Saiboku-to, Sairei-to, Juzen-taiho-to, Jumi-haidoku-to, Juncho-to, Nyoshin-san, Shoma-kakkon-to, Sho-kenchu-to, Sho-saiko-to-ka-kikyo-sekko, Sho-saiko-to, Sho-saiko-to-go-keishi-ka-shakuyaku-to, Sho-saiko-to-kyo-shokyo-ka-oren-bukuryo, Sho-seiryu-to, Sho-hange-ka-bukuryo-to, Shofu-san, Shimbu-to, Shimpi-to, Shin'i-seihai-to, Ninjin-to, Ninjin-yoei-to, Seisho-ekki-to, Seijo-bofu-to, Seishin-renshi-in, Seihai-to, Senkyu-chacho-san, Sokei-kakketsu-to, Zokumei-to, Daio-botampi-to, Daio-kanzo-to, Dai-kenchu-to, Dai-joki-to, Dai-bofu-to, Chikujo-untan-to, Chorei-to-go-shimotsu-to, Chorei-to, Choi-joki-to, Tsu-do-san, Choto-san, Tokaku-joki-to, Toki-inshi, Toki-kenchu-to, Toki-shigyaku-ka-goshuyu-shokyo-to, Toki-to, Toki-shakuyaku-san, Nichin-to, Nijutsu-to, Haino-san-kyu-to, Byakko-kaninjin-to, Bakumondo-to, Hachimi-jio-gan, Hange-koboku-to, Hange-byakujutsu-temma-to, Hange-shashin-to, Heii-san, Hochu-ekki-to, Bofu-tsu-sho-san, Boi-ogi-to, Ma-kyo-kan-seki-to, Makyo-yoku-kan-to, Mao-to, Mao-bushi-saishin-to, Mashinin-gan, Moku-boi-to, Yoku-kan-san, Yoku-kan-san-ka-chimpi-hange, Rikko-san, Ryutan-shakan-to, Ryo-kan-kyo-mi-shin-ge-nin-to, Ryo-kei-jutsu-kan-to, Ryo-kyo-jutsu-kan-to, Rikkunshi-to, Rokumi-gan, Sha-kanzo-to, Shakuyaku-kanzo-to, Inchin-gorei-san, Inchinko-to, Bukuryo-in-go-hange-koboku-to, Bukuryo-in, Kyuki-kyogai-to and Yokuinin-to.

Examples of Kampo medicines which are particularly suitable for the present invention include Oren-gedoku-to, Sho-saiko-to, Ninjin-to, San'o-shashin-to, Mao-bushi-saishin-to, Anchu-san, Keishi-bukuryo-gan, Byakko-ka-ninjin-to, Shakuyaku-kanzo-to and Sairei-to.

Examples of crude drugs to be used in the present invention are described, for example, in *Genshoku Wakanyaku Zukan* (*Heliotype Picture Book of Japanese and Chinese Medicines*) (volumes I and II, Tsuneo Nanba, published by Hoikusha K. K., Apr. 1, 1970) and *Dai 12-kaisei Nihon Yakkyokuho Kaisetsusho* (*Manual for the 12th Edition of Pharmacopoeia of Japan*) (supervised by Nippon Koteisho Kyokai, published by Hirokawa Shoten K. K.).

The powdered extract of the above-mentioned Kampo medicines or crude drugs may be obtained by a conventional method employed for producing powdered extracts. That is to say, crude drugs required for preparation of the desired Kampo medicine or crude drug preparation are cut into pieces, weighed, extracted, concentrated and dried to obtain the powdered extract.

Examples of the solvent for extracting Kampo medicines include water, ethanol and acetic acid. Either hot-extraction or cold-extraction may be employed, particularly, hot-extraction (90° to 100° C.) with water is preferable.

The extract solution is usually concentrated under reduced pressure, i.e., under a pressure of from 30 to 760 mmHg and at an evaporation temperature of 100° C. or below, preferably from 30° to 50° C.

The above-mentioned extract solution or a concentrate thereof is then dried by a method commonly employed in the art (for example, spray-drying, vacuum-drying and freeze-drying) to thereby give a Kampo medicine powdered extract.

In the case of spray-drying, the extract solution or its concentrate may be sprayed into a hot air stream in a drying room maintained at a high temperature (60° to 300° C.). Thus the solvent may be instantaneously evaporated and the aimed powdered extract may be obtained. Typical examples of the method for contacting the sprayed droplets with the hot air stream include parallel flow type, counter flow type and mixed flow type systems. Examples of the method for converting the liquid into fine droplets include centrifugal, pressurized-spraying and binary-nozzle systems.

In the case of vacuum-drying, the extract solution may be sufficiently concentrated under reduced pressure and then dried under a pressure of 760 mmHg or below at a temperature of from 5° to 100° C.

In the case of freeze-drying, the extract solution or its concentrate may be frozen by cooling at −80° to 0° C. and then the solvent is directly sublimated under a pressure of 1 mmHg or below so as to give the desired powdered extract.

In the preparation of a Kampo medicine powdered extract, appropriate fillers may be used as carriers in such an amount that the additives do not prevent the pharmaceutical effect of the Kampo medicine hard capsules. Examples of such fillers include starch, dextrin, lactose, sucrose, mannitol, crystalline cellulose and anhydrous silicic acid. The fillers to be used as carriers may be dissolved or dispersed by any means without restriction, so long as they can be homogeneously dissolved or dispersed in the solvent, for example, an appropriate stirrer may be used therefor.

In addition, conventional additives such as binders, disintegrating agents, surfactants, corrigents and perfumes may be added in such an amount that the additives do not prevent the pharmaceutical effect of the Kampo medicine hard capsules, if needed.

As binders, powdered acacia, gelatin, hydroxypropyl starch, methylcellulose, carboxymethylcellulose sodium, hydroxypropyl-cellulose, ethylcellulose, polyvinylpyrrolidone and macrogol are illustrated.

As disintegrating agents, starch, hydroxypropyl starch, carboxymethylcellulose sodium, carboxymethylcellulose, low-substituted hydroxy-propylcellulose and carboxymethylcellulose calcium are illustrated.

As surfactants, sodium lauryl sulfate, soybean lecithin, sucrose fatty acid esters and polysorbate 80 are illustrated.

As lubricants, talc, waxes, hydrogenated vegetable oils, sucrose fatty acid esters, magnesium stearate, calcium stearate, aluminum stearate, polyethylene glycol, light anhydrous silicic acid, dried aluminum hydroxide gel, synthetic aluminum silicate and magnesium silicate are illustrated.

The powder thus obtained may be then compacted with the use of a roller compacter, a briquette machine or a slug tableting press, followed by crushing.

The particle size of the granules thus obtained may be arbitrarily selected, so long as the granules can be filled in hard gelatin capsules. For example, Kampo medicine granules of a high specific gravity dressed through 10-mesh (1.7 mm) to 200-mesh (75 μm) sieves may be obtained.

To the granules thus obtained, from 0.01 to 5%, preferably from 0.5 to 3.0%, by weight, of magnesium stearate is added and then the resulting mixture is filled in hard gelatin capsules, to obtain the Kampo medicine hard capsules.

Magnesium stearate has been used as a lubricant or a fluidization accelerator in the preparation of pharmaceutical composition in the form of tablets. However, there has never been reported to use this substance for improving dissolution properties of Kampo medicine hard capsules until the present inventors have achieved this finding.

To further illustrate the present invention in greater detail, and not by way of limitation, the following Examples based on the production process of the present invention will be given.

EXAMPLE 1

To 10 kg of a crude drug preparation of Oren-gedokuto (3 parts of Scutellaria Root, 2 parts of Coptis Rhizome, 2 parts of Gardenia Fruit and 1.5 parts of Phellodendron Bark), 200 l of water was added followed by hot-extracting at 100° C. Following the extraction, hot solid/liquid separation was performed and thus an extract solution was obtained. This extract solution was concentrated and spray dried (blowing air temperature: 160° C., exhaust air temperature: 110° C.) to obtain an Oren-gedoku-to powdered extract.

Thus obtained Oren-gedoku-to powdered extract (200 parts) was mixed with 1 part of silicon dioxiside ("AEROSIL 200" manufactured by Nippon Aerosil K. K.) and compression-molded followed by crushing and classifying to obtain granules of 0.5 to 1.4 mm in particle size. Thus obtained granules (100 parts) were mixed with 1 part of magnesium stearate and the mixture filled in gelatin capsules No.2 to obtain Oren-gedoku-to hard capsules each weighing 315 mg (Invention Capsule 1).

EXAMPLE 2

To 10 kg of a crude drug preparation of Sho-saiko-to (7 parts of Bupleurum Root, 5 parts of Pinellia Tuber, 3 parts of Scutellaria Root, 3 parts of Jujube Fruit, 3 parts of Ginseng Root, 2 parts of Glycyrhiza Root and 1 part of Ginger Rhizome), 200 l of water was added followed by hot-extracting at 100° C. Following the extraction, hot solid/liquid separation was performed and thus an extract solution was obtained. This extract solution was concentrated and spray dried (blowing air temperature: 160° C., exhaust air temperature: 100° C.) to obtain a Sho-saiko-to powdered extract.

Thus obtained Sho-saiko-to powdered extract (200 parts) was mixed with 1 part of silicon dioxide ("AEROSIL 200") and 2 parts of magnesium stearate, and the mixture compression-molded. After crushing and classifying, Sho-saiko-to extract granules of 0.5 to 1.4 mm in particle size were obtained. The granules thus obtained (100 parts) were mixed with 2 part of magnesium stearate and then the mixture filled in gelatin capsules No.0 to obtain Sho-saiko-to hard capsules each weighing 600 mg (Invention Capsule 2).

EXAMPLE 3

To 10 kg of a crude drug preparation of Ninjin-to (3 parts of Glycyrrhiza Root, 3 parts of Atractylodes Lancea Rhizome, 3 parts of Ginseng Root and 3 parts of Dried Ginger Rhizome), 200 l of water was added followed by hot-extracting at 100° C. Following the extraction, hot solid/liquid separation was performed and thus an extract solution was obtained. This extract solution was concentrated and spray dried (blowing air temperature: 150° C., exhaust air temperature: 100° C.) to obtain a Ninjin-to powdered extract.

Thus obtained Ninjin-to powdered extract (500 parts) was mixed with 1 part of silicon dioxide ("AEROSIL 200") and 5 parts of magnesium stearate, and the mixture compression-molded. After crushing and classifying, Ninjin-to extract granules of 0.35 to 1.4 mm in particle size were obtained. The granules thus obtained (100 parts) were mixed with 1 part of magnesium stearate and then the mixture filled in gelatin capsules No.1 to obtain Ninjin-to hard capsules each weighing 407 mg (Invention Capsule 3).

EXAMPLE 4

To 10 kg of a crude drug preparation of San'o-shashin-to (3 parts of Scutellaria Root, 3 parts of Coptis Rhizome and 3 parts of Rhubarb Rhizome), 200 l of water was added followed by hot-extracting at 100° C. Following the extraction, hot solid/liquid separation was performed and thus an extract solution was obtained. This extract solution was concentrated and spray dried (blowing air temperature: 150° C., exhaust air temperature: 100° C.) to obtain a San'o-shashin-to powdered extract.

Thus obtained San'o-shashin-to powdered extract (100 parts), 5 parts of carboxymethylcellulose calcium (manufactured by Gotoku Yakuhin K. K., the same will apply hereinafter) and 0.3 parts of magnesium stearate were mixed together and the mixture compression-molded. After crushing and classifying, San'o-shashin-to extract granules of 0.35 to 1.4 mm in particle size were obtained. Thus obtained granules (100 parts) were mixed with 0.7 part of magnesium stearate and the mixture filled in gelatin capsules No.1 to obtain San'o-shashin-to hard capsules each weighing 388 mg.

EXAMPLE 5

To 1 kg of a crude drug preparation of Mao-bushi-saishin-to (4 parts of Ephedra Herb, 3 parts of Asiasarum Root and 1 part of Processed Aconite Tuber), 20 l of water was added followed by hot-extracting at 100° C. Following the extraction, hot solid/liquid separation was performed and thus an extract solution was obtained. This extract solution was concentrated and freeze-dried (freezing temperature: −40° C., degree of vacuum: 0.1 Torr, shelf temperature: 20° C.) to obtain a Mao-bushi-saishin-to powdered extract.

Thus obtained Mao-bushi-saishin-to powdered extract (100 parts) and 3 parts of carboxymethylcellulose calcium were mixed together and the mixture compression-molded. After crushing and classifying, Mao-bushi-saishin-to extract granules of 0.15 to 1.0 mm in particle size were obtained. The granules thus obtained (100 parts) were mixed with 1 part of magnesium stearate and then the mixture filled in gelatin capsules No.2 to obtain Mao-bushi-saishin-to hard capsules each weighing 323 mg (Invention Capsule 4).

EXAMPLE 6

To 1 kg of a crude drug preparation of Anchu-san (4 parts of Cinnamon Bark, 3 parts of Corydalis Tuber, 3 parts of Oyster Shell, 1.5 parts of Fennel Fruit, 1.0 part of Glycyrrhiza Root, 1.0 part of Amomum Seed and 0.5 part of Galanga Rhizome), 20 l of water was added followed by hot-extracting at 100° C. Following the extraction, hot solid/liquid separation was performed and thus an extract solution was obtained. This extract solution was concentrated and freeze-dried (freezing temperature: −40° C., degree of vacuum: 0.1 Torr, shelf temperature: 20° C.) to obtain an Anchu-san powdered extract.

Thus obtained Anchu-san powdered extract (100 parts) and 3 parts of carboxymethylcellulose calcium were mixed together and the mixture compression-molded. After crushing and classifying, Anchu-san extract granules of 0.15 to 1.0 mm in particle size were obtained. The granules thus obtained (100 parts) were mixed with 1 part of magnesium stearate and the mixture filled in gelatin capsules No.2 to obtain Anchu-san hard capsules each weighing 323 mg (Invention Capsule 5).

EXAMPLE 7

To 10 kg of a crude drug preparation of Keishi-bukuryo-gan (3 parts of Cinnamon Bark, 3 parts of Peony Root, 3 parts of Peach Kernal, 3 parts of Hoelen and 3 parts of Moutan Bark), 200 l of water was added followed by hot-extracting at 100° C. Following the extraction, hot solid/liquid separation was performed and thus an extract folution was obtained. This extract solution was concentrated and spray dried (blowing air temperature: 160° C., exhaust air temperature: 110° C.) to obtain a Keishi-bukuryo-gan powdered extract. Thus obtained Keishi-bukuryo-gan powdered extract (200 parts), 20 parts of low-substituted hydroxypropylcellulose ("LHPC LH-11", manufactured by Shin-Etsu Chemical, Co., Ltd.) and 1 part of light anhydrous silicic acid (Syloid 266, manufactured by Fuji-Davison K. K.) were mixed together and the mixture compression-molded. After crushing and classifying, Keishi-bukuryo-gan extract granules of 0.3 to 1.2 mm in particle size were obtained. The granules thus obtained (100 parts) were mixed with 1 part of magnesium stearate and then the mixture filled in gelatin capsules No.2 to obtain Keishi-bukuryo-gan hard capsules each weighing 300 mg (Invention Capsule 6).

EXAMPLE 8

To 10 kg of a crude drug preparation of Byakko-ka-ninjin-to (15 parts of Gypsum, 5 parts of Anemarrhena Rhizome, 2 parts of Glycyrrhiza Root, 1.5 parts of Ginseng Root and 8 parts of Oryza Seed), 100 l of water was added followed by hot-extracting at 100° C. Following the extraction, hot solid/liquid separation was performed and thus an extract solution was obtained. This extract solution was concentrated and spray dried (blowing air temperature: 160° C., exhaust air temperature: 100° C.) to obtain a Byakko-ka-ninjin-to powdered extract. Thus obtained Byakko-ka-ninjin-to powdered extract (200 parts), 1 part of light anhydrous silicic acid ("Syloid 266", manufactured by Fuji-Davison K. K.) and 2 parts of magnesium stearate were mixed together and the mixture compression-molded. After crushing and classifying, Byakko-ka-ninjin-to granules of 0.3 to 1.2 mm in particle size were obtained. The granules thus obtained (100 parts) were mixed with 1 part of magnesium stearate and then the mixture filled in gelatin capsules No.2 to obtain Byakko-ka-ninjin-to hard capsules each weighing 280 mg (Invention Capsule 7).

EXAMPLE 9

To 10 kg of a crude drug preparation of Shakuyaku-kanzo-to (6 parts of Glycyrrhiza Root and 6 parts of Peony Root), 120 l of water was added followed by hot-extracting at 100° C. Following the extraction, hot solid/liquid separation was performed and thus an extract solution was obtained. This extract solution was concentrated and spray dried (blowing air temperature: 160° C., exhaust air temperature: 100° C.) to obtain a Shakuyaku-kanzo-to powdered extract. Thus obtained Shakuyaku-kanzo-to powdered extract (200 parts), 10 parts of low-substituted hydroxypropylcellulose ("LHPC LH-11", manufactured by Shin-Etsu Chemical, Ltd.), 1 part of light anhydrous silicic acid ("Syloid 266", manufactured by Fuji-Davison K. K.) and 1 part of magnesium stearate were mixed together and the mixture compression-molded. After crushing and classifying, Shakuyaku-kanzo-to granules of 0.3 to 1.2 mm in particle size were obtained. The granules thus obtained (100 parts) were mixed with 0.5 part of magnesium stearate and the mixture filled in gelatin capsules No.2 to obtain Shakuyaku-kanzo-to hard capsules each weighing 340 mg (Invention Capsule 8).

EXAMPLE 10

To 10 kg of a crude drug preparation of Sairei-to (7 parts of Bupleurum Root, 5 parts of Alisma Rhizome, 5 parts of Pinellia Tuber, 3 parts of Scutellaria Root, 3 parts of Atractylodes Lancea Rhizome, 3 parts of Jujube Fruit, 3 parts of Chuling, 3 parts of Ginseng Root, 3 parts of Hoelen, 2 parts of Glycyrrhiza Root, 2 parts of Cinnamon Bark and 1 part of Ginger Rhizome), 200 l of water was added followed by hot-extracting at 100° C. Following the extraction, hot solid/liquid separation was performed and thus an extract solution was obtained. This extract solution was concentrated and spray dried (blowing air temperature: 160° C., exhaust air temperature: 110° C.) to obtain a Sairei-to powdered extract. The above-mentioned Sairei-to powdered extract (200 parts) and 1 part of magnesium stearate were mixed together and the mixture compression-molded. After crushing and classifying, Sairei-to granules of 0.3 to 1.2 mm in particle size were obtained. The granules thus obtained (100 parts) were mixed with 1 part of magnesium stearate and then the mixture filled in gelatin capsules No.2 to obtain Sairei-to hard capsules each weighing 315 mg (Invention Capsule 9).

The following Test Examples will be given in order to show the excellent dissolution properties of the Kampo medicine hard capsules obtained by the present invention.

TEST EXAMPLE 1

The procedure of Example 1 was repeated except that no magnesium stearate was added to the extract granules to obtain Oren-gedoku-to hard capsules each weighing 313 mg (Comparative Capsule 1).

The dissolution times of Invention Capsule 1 obtained in Example 1 and Comparative Capsule 1 were measured.

The dissolution properties of these capsules were examined by the dissolution test (paddle test) specified in the 12th Edition of Pharmacopoeia of Japan.

Namely, 900 ml of purified water was introduced into a glass vessel (1,000 ml) having a hemispherical bottom (inner diameter: 100 mm, height: 160 mm, diameter 50 mm) and the temperature of the liquid was maintained at 37±0.5° C.

A helical acid-resistant wire (wire diameter: 1 mm, inner diameter: 12 mm, length 25 mm, winding interval: 3 mm) was fixed with the use of 10 acid-resistant supporting wires (wire diameter: 1 mm) located in parallel around the outer periphery. Each side was fixed with two crossed wires and thus a sinker was formed. In this sinker, Invention Capsule 1 and Comparative Capsule 1 were introduced and sunk toward the bottom of the test reactor. Then these capsules were stirred at 100 r.p.m. with a puddle consisting of acid-resistant blades and a rotating shaft.

The eluate was collected to determine the content of the active ingredient at appropriate intervals and the time required for achieving the content of the active ingredient in the sampled eluate of 75% based on that after the completion of the dissolution was referred to as the elution time ($T_{75\%}$).

As a result, it was confirmed that the dissolution time of Comparative Capsule 1 was 120 minutes while that of Invention Capsule 1 was 13 minutes, which indicated that the latter quickly liberated the active ingredient.

TEST EXAMPLE 2

The procedure of Example 2 was repeated except that no magnesium stearate was added to the extract granules to obtain Sho-saiko-to hard capsules each weighing 590 mg (Comparative Capsule 2).

The dissolution times of Invention Capsule 2 obtained in Example 2 and Comparative Capsule 2 were measured by the same method as in Test Example 1. As a result, it was confirmed that the dissolution time of Comparative Capsule 2 was 80 minutes while that of Invention Capsule 2 was 15 minutes, which indicated that the latter quickly liberated the active ingredient.

TEST EXAMPLE 3

The procedure of Example 3 was repeated except that no magnesium stearate was added to the extract granules to obtain Ninjin-to hard capsules each weighing 404 mg (Comparative Capsule 3).

The dissolution times of Invention Capsule 3 obtained in Example 3 and Comparative Capsule 3 were measured by the same method as in Test Example 1. As a result, it was confirmed that the dissolution time of Comparative Capsule 3 was 52 minutes while that of Invention Capsules 3 was 18 minutes, which indicated that the latter quickly liberated the active ingredient.

TEST EXAMPLE 4

The procedure of Example 5 was repeated except that no magnesium stearate was added to the extract granules to obtain Mao-bushi-saishin-to hard capsules each weighing 320 mg (Comparative Capsules 4).

The dissolution times of Invention Capsule 4 obtained in Example 5 and Comparative Capsule 4 were measured by the same method as in Test Example 1. As a result, it was confirmed that the dissolution time of Comparative Capsule 4 was 85 minutes while that of Invention Capsule 4 was 14 minutes, which indicated that the latter quickly liberated the active ingredient.

TEST EXAMPLE 5

The procedure of Example 6 was repeated except that no magnesium stearate was added to the extract granules to obtain Anchu-san hard capsules each weighing 321 mg (Comparative Capsules 5).

The dissolution times of Invention Capsule 5 obtained in Example 6 and Comparative Capsule 5 were measured by the same method as in Test Example 1. As a result, it was confirmed that the dissolution time of Comparative Capsule 5 was 50 minutes while that of Invention Capsule 5 was 17 minutes, which indicated that the latter quickly liberated the active ingredient.

TEST EXAMPLE 6

The procedure of Example 7 was repeated except that compression-molding was not conducted to obtain Keishi-bukuryo-gan capsules each weighing 300 mg (Comparative Capsule 6).

The dissolution times of Invention Capsule 6 obtained in Example 7 and Comparative Capsule 6 were measured by the same method as in Test Example 1. As a result, it was confirmed that the dissolution time of Comparative Capsule 6 was longer than 60 minutes while that of Invention Capsule 6 was 8 minutes, which indicated that the latter quickly liberated the active ingredient.

TEST EXAMPLE 7

The procedure of Example 8 was repeated except that no magnesium stearate was added to the extract granules to obtain Byakko-ka-ninjin-to capsules each weighing 278 mg (Comparative Capsule 7).

The dissolution times of Invention Capsule 7 obtained in Example 8 and Comparative Capsule 7 were measured by the same method as in Test Example 1. As a result, it was confirmed that the dissolution time of Comparative Capsule 7 was 50 minutes while that of Invention Capsules 7 was 20 minutes, which indicated that the latter quickly liberated the active ingredient.

TEST EXAMPLE 8

The procedure of Example 9 was repeated except that compression-molding was not conducted to obtain Shakuyaku-kanzo-to capsules each weighing 340 mg (Comparative Capsule 8).

The dissolution times of Invention Capsule 8 obtained in Example 9 and Comparative Capsule 8 were measured by the same method as in Test Example 1. As a result, it was confirmed that the dissolution time of Comparative Capsule 8 was 60 minutes while that of Invention Capsule 8 was 7 minutes, which indicated that the latter quickly liberated the active ingredient.

TEST EXAMPLE 9

The procedure of Example 10 was repeated except that compression-molding was not conducted to obtain Sairei-to capsules each weighing 315 mg (Comparative Capsule 9).

The dissolution times of Invention Capsule 9 obtained in Example 10 and Comparative Capsule 9 were measured by the same method as in Test Example 1. As a result, it was confirmed that the dissolution time of Comparative Capsule 9 was longer than 60 minutes while that of Invention Capsule 9 was 11 minutes, which indicated that the latter quickly liberated the active ingredient.

According to the present invention, Kampo medicine hard capsules having a high Kampo medicine extract content and showing good dissolution properties, with the elution time ($T_{75\%}$) being not longer than 30 minutes when measured according to the dissolution test (paddle test) specified in the 12th Edition of Pharmacopoeia of Japan, can be obtained.

While the present invention has been described in conjunction with specific embodiments thereof, it is evident that many alternatives, modifications and variations will be apparent to those skilled in the art in light of the foregoing description. Accordingly, it is intended to include all such alternatives, modifications and variations as set forth within the spirit and scope of the appended claims.

What is claimed is:

1. A process for producing Kampo medicine hard capsules, which comprises compacting Kampo medicine extract powder, mixing magnesium stearate with the compacted Kampo medicine extract powder and filling the mixture into gelatin hard capsules.

2. A process as in claim 1, wherein the weight ratio of said magnesium stearate to said compacted Kampo medicine extract powder ranges from 0.5/100 to 3/100.

3. A process as in claim 1, wherein said Kampo medicine is selected from the group consisting of Orengedoku-to, Sho-saiko-to, Ninjin-to, San'o-shashin-to, Mao-bushi-saishin-to, Anchu-san, Keishi-bukuryo-gan, Byakko-ka-ninjin-to, Shakuyaku-kanzo-to and Sairei-to.

* * * * *